United States Patent [19]
Herron et al.

[11] Patent Number: 5,654,500
[45] Date of Patent: Aug. 5, 1997

[54] METHOD FOR DETERMINING CYCLIC SERVICE LIFE FOR ROTATIONAL PARTS OF A ROTARY MACHINE

[75] Inventors: William Lee Herron, Greer; Thomas Joseph Martini, Greenville, both of S.C.

[73] Assignee: General Electric Co., Schenectady, N.Y.

[21] Appl. No.: 633,330

[22] Filed: Apr. 17, 1996

[51] Int. Cl.[6] .................................................. G01N 3/00
[52] U.S. Cl. ............................................... 73/116; 73/117.3
[58] Field of Search ........................... 73/112, 116, 117.1, 73/117.2, 117.3, 865.9

[56] References Cited

U.S. PATENT DOCUMENTS

| | | | |
|---|---|---|---|
| 4,046,002 | 9/1977 | Murphy et al. | 73/116 |
| 4,203,705 | 5/1980 | Wesbecher | 416/95 |
| 4,280,185 | 7/1981 | Martin | 73/112 |
| 5,042,295 | 8/1991 | Seeley | 73/117.3 |

*Primary Examiner*—George M. Dombroske
*Assistant Examiner*—Max H. Noori
*Attorney, Agent, or Firm*—Nixon & Vanderhye

[57] ABSTRACT

Total transient stress, which is the sum of residual, mechanical and thermal stresses, is calculated. Transient stresses are estimated using compressor discharge temperature and pressure, the rotational speed of the component and the elapsed time from the beginning of a transient. By using a general stress calculation, the total stress at the end of transients at each location in the rotary part being measured can be calculated. Maximum and minimum stress peaks are recorded for the transients and stress intensity factors for each location are calculated. Crack propogation is then calculated based on the stress intensity factors and the remaining life of the machine can then be calculated using new assumed crack length and design cycle of the machine.

8 Claims, 6 Drawing Sheets

1

METHOD FOR DETERMINING CYCLIC SERVICE LIFE FOR ROTATIONAL PARTS OF A ROTARY MACHINE

TECHNICAL FIELD

The present invention relates to a method for determining cyclic service life for rotating parts of a machine and particularly relates to a method for assessing the severity of an actual duty cycle on the rotating parts of a machine, e.g., a turbine, relative to a calculated or assumed cycle to determine its effect on remaining calculated cyclic life whereby the remaining and, hence, useful cyclic life of the rotary machine can be determined.

BACKGROUND

In the design of any machine, and particularly a machine having rotating parts, there is an anticipated finite life expectancy for the machine in terms of the number of duty cycles through which the machine may operate. That is because rotating components in the machine are subject to varying mechanical and thermal loadings, oftentimes severe. For example, in the case of turbines, the design of the machine includes a calculation of its operating life. A complete duty cycle typically includes operation between on and off cycles for the machine. For example, a complete duty cycle for design purposes assumes the machine is initially started and takes a certain time to attain full speed, a load is applied, the machine is maintained under full or partial load, the load is removed, and the machine coasts down to zero speed and stops. A cycle of this type is fairly representative of actual use of a machine, such as a turbine, in the field.

The actual duty cycle of a machine, however, differs from the assumed or calculated cycle. That is, customers may operate their machinery in modes considerably different than assumed during the design of the machine. Consequently, the assumed or design cycle may be too liberal, involving risk of component failure, or too conservative, such as to understate the anticipated life of the machine. Consequently, if the actual duty cycle can be monitored and its actual severity ascertained, its effect on the remaining cyclic life of the machine can be established and, hence, the calculated useful life of the machine can be more accurately predicted in a given installation.

DISCLOSURE OF THE INVENTION

According to the present invention, parameters of the machine are monitored during an actual duty cycle to establish its severity relative to the assumed or calculated design cycle whereby a prediction of the useful life of the machine is obtained. Particularly, the present invention enables the determination of the total transient stress at each of a plurality of given locations within a rotating part of the machine. The total stress is the sum of the residual, mechanical and thermal stresses at each location. The residual stress is a constant for a given rotating part location and may be assumed to be uniform. The mechanical stress is established by multiplying a calculated, known isothermal stress in the rotating part at the particular location by the square of the ratio of actual speed to the speed used in the design stress calculation. Thus, the mechanical stress is a function of a constant multiplied by the square of the ratio of the actual-to-design speeds. A principal feature of the present invention resides in the recognition that in the rotating parts of a machine, for example, a turbine, the thermal environment is dominated by air flow directly proportional to compressor discharge temperatures and pressures and that therefore transient stresses may be estimated using only compressor discharge temperature and pressure, the actual rotational speed of the component and the elapsed time from the beginning of the transient. It is also based on the recognition that the duty cycle can be treated as a continuous series of interrupted transients, each lasting for only a sampling time interval. Employing these concepts, the total stress remaining from a previous duty cycle is determined as the starting total stress at the beginning of the next duty cycle. If the time interval between the end of the previous duty cycle and the beginning of the next duty cycle is greater than the time necessary for the thermal stress to reach steady state, then the steady state stress at the beginning of the next duty cycle equals the residual stress. However, if the time interval between the end of the previous duty cycle and the beginning of the next duty cycle is less than the time necessary for the thermal stress to reach steady state, then the total stress at the start of the next duty cycle ($\sigma_{tot_0}$) is the thermal stress at the beginning of the previous shutdown transient multiplied by the ratio of the time interval between the duty cycles to the time required for the thermal stress of the previous transient to reach steady state, plus the residual stress. The steady state thermal stress for the start-up of the next duty cycle $\sigma_{ss_1}$ is a function of measured compressor discharge temperature, and the time to reach that steady state stress ($t_{ss_1}$) is a function of compressor discharge pressure and temperature as well as measured speed of rotation. The total stress at the start of the next duty cycle ($\sigma_{tot_1}$), is $\sigma_{tot_0}$ plus the mechanical stress calculated as above. The time ($t_{ss_1}$) required for the transient stress to equal the steady state stress $\sigma_{ss_1}$ of that startup can be calculated and recorded in memory with $\sigma_{tot_0}$, $\sigma_{tot_1}$, and $\sigma_{ss_1}$.

After a predetermined time interval from the start of the extant duty cycle, the compressor discharge temperature and pressure, as well as the speed of rotation of each part being subjected to the thermal stress analysis, and the time interval is measured. By using a general stress calculation set forth in detail in the following description, the total stress at the end of the predetermined time interval (the first transient in the extant duty cycle) at each location in the rotary part being measured can be calculated. If the difference in the total stress at the end of the first transient ($\sigma_{tot_2}$) and the total stress at the end of the previous duty cycle ($\sigma_{tot_0}$) is greater than the difference between the total stresses at the beginning of the new duty cycle ($\sigma_{tot_1}$) and the end of the previous duty cycle ($\sigma_{tot_0}$), the new total stress is recorded, overwriting $\sigma_{tot_1}$. If, however, the difference in total stress at the end of the first transient of the new duty cycle and the total stress at the end of the previous duty cycle is less than or equal to the difference between the total stress at the beginning of the duty cycle and the stress at the end of the previous duty cycle, the total stress at the beginning of the new duty cycle is retained in memory. Additionally, the total stress at the end of the time interval of the new duty cycle is recorded. Consequently, the prior peak stress and the possible new minimum stress is retained in memory.

After another time interval, the compressor temperature and pressure and actual speed of rotation is measured at each rotary location. Thermal stress calculations based on those measurements are made.

As a consequence, there are recorded maximum and minimum stress peaks for the time intervals (transients) within the duty cycle. It will be appreciated that if the maximum stress peak at the end of a given time interval (transient) is less than the maximum stress peak of the next time interval, the given maximum stress need not be recorded. Similarly, if a minimum stress peak for a given time interval is registered and a lower minimum peak is registered in the next time interval, the prior minimum stress peak need not be remembered or retained in the buffer. Knowing the recorded maximum and minimum stress peaks at the various time intervals, stress intensity factors for each location are calculated for that duty cycle. The stress intensity factor is a function of the stress range between the maximum and minimum recorded stresses and the radius of an assumed crack. The crack propagation is then calculated based on the stress intensity factors. The remaining life of the machine can then be calculated using the new assumed crack length and the design cycle of the machine. As used herein, the terms "most extreme" and "less extreme" depend upon the trend of the stress values for time intervals prior to the one being recorded. For example, if the stresses were increasing with time and the current stress is higher than the prior reading, that current stress is "more extreme." Similarly, if the stresses were decreasing with time and the current stress is lower than the prior reading, that current stress is "more extreme." If the stresses were increasing and current stress is lower than the prior stress, then it is "less extreme" and the prior stress established a maximum value. Similarly, if the stresses have been decreasing and the current stress is higher than the prior stress, then it is "less extreme" and the prior stress established a minimum value.

In a preferred embodiment according to the present invention, there is provided a process for determining cyclic service life for rotational parts of a turbine having a compressor comprising the steps of (a) measuring compressor discharge pressure and temperature and speed of a rotational part of the turbine at the end of each of a plurality of time intervals in and commencing at the start of a duty cycle, (b) determining the total stress on the rotational part at the end of each time interval based on values of the measured pressure, temperature and part speed; (c) recording, for each time interval, either (i) the total stress on the part as a maximum or minimum value if the total stress for a given time interval is more extreme than a last recorded total stress of a preceding time interval or (ii) the last recorded total stress as a maximum or minimum value if the total stress on the part in the given time interval is less extreme than the last recorded total stress and, if the total stress of Paragraph (c)(ii) is recorded, the total stress on the part as a new minimum or maximum value for the given time interval; (d) at the end of the duty cycle, determining stress intensity factors using the previously recorded maximum and minimum values of the total stresses, (e) determining from the stress intensity factors, an aggregate propagation value of an assumed crack for the duty cycle and (f) determining a remaining calculated cyclic life for the machine based on the aggregate crack propagation, Accordingly, it is a primary object of the present invention to provide a novel and improved method for monitoring the cyclic service life of rotating parts of a machine, for example, a turbine to establish a remaining cyclic life based on a comparison of the design or calculated duty cycle and the stresses incurred in the rotating parts through the actual duty cycles.

BEST MODE FOR CARRYING OUT THE INVENTION

Figure 1:
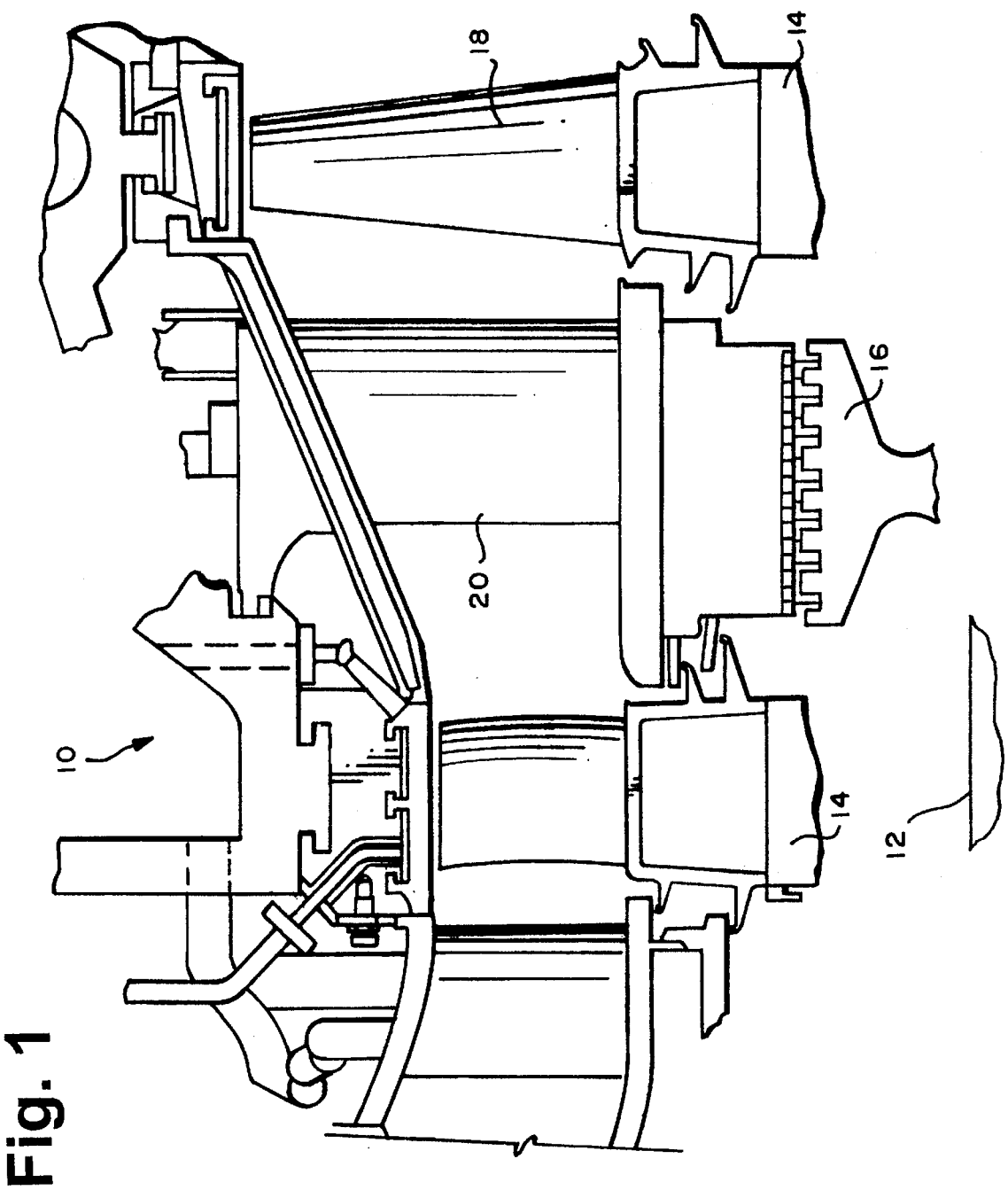
FIG. 1 is a schematic illustration of a portion of a turbine with which the present invention may be utilized.

Referring now to the drawings, there is illustrated in FIG. 1 a rotary machine, e.g., a turbine or compressor (here, a turbine for purposes of illustration), generally designated 10, having a rotor shaft 12 mounting turbine wheels 14 and disks 16 between the turbine wheels, all rotatable about a turbine axis. The turbine wheels mount turbine buckets 18, forming, in conjunction with stator blades 20, various stages of the turbine. In accordance with the present invention, the severity of the thermal stress during actual operating conditions for the rotating parts of the machine, for example, the wheels and rotor, can be calculated. The present invention is particularly useful for monitoring the wheels and shaft which are exposed to well-defined conditions that can be related entirely to compressor discharge outlet conditions, i.e., the rotor is exposed to compressor bleed air. In accordance with the present invention, cracks are assumed at various locations of the rotating parts, e.g., at one or more radii at circumferentially spaced locations about a wheel 14 or a disk 16. For a given duty cycle, the extent to which that crack will grow or propagate can be calculated. Once the extent of crack propagation is calculated, a comparison of the severity of the actual duty cycle with the calculated design severity for the machine is made, a new calculation of the remaining cyclic life of the machine can be obtained. That is, to the extent the actual duty cycle varies from the design duty cycle, the cyclic life for the machine remaining after each duty cycle can be predicted in relation to the design cycle. Fundamentally, to calculate the severity of the actual duty cycle, the total stress at the various locations of the part being subjected to the analysis can be determined throughout the actual duty cycle. By recording the maximum and minimum peaks of the total stress, a calculation of the growth of the presumed crack during the actual duty cycle can be obtained. By comparing the calculated crack growth for an actual duty cycle and the design life cycle calculation, the calculated number of design life cycles left in the machine can be determined. Stated differently, the actual severity of a given duty cycle of the machine is compared with the design cycle life so that the life cycles remaining in the machine can be calculated, depending upon the history of actual usage of the machine.

As used in the present specification, the following terms are defined:

i—A running count of the number of distinct transients in the duty cycle

R—Ratio of minimum to maximum cyclic stress

ΔR—Growth of assumed crack

RA—Radius of initially assumed crack plus growth of assumed crack ΔR

TCD or T—Compressor discharge temperature

PCD or P—Compressor discharge pressure

N—Rotor speed t—Time $\sigma_{ss}$—Steady state stress at end of transient $\sigma_0$—Stress at start of transient $\sigma_{trans}$—Transient thermal stress a—A multiplier proportional to heat transfer coefficient j—A running count of the stress peaks recorded during the duty cycle $t_{ss}$—Time required for $\sigma_{trans} \approx \sigma_{ss}$ $\sigma_{res}$—Residual stress $\sigma_{mech}$—Mechanical stress $\sigma_{tot}$—Total stress $\sigma_{peak}$—Peak stress experienced in a transient b—A thermal stress severity constant $t_{peak}$—Time required for the transient stress to equal $\sigma_{peak}$ W—Walker multiplier L—A TCD below which Ao is insignificant s—Length of time in time interval NR—Propagation life of assumed crack at each location subjected to analysis P—Subscript indicating initial conditions for design duty cycle $K_p$—Stress intensity factor for initially assumed crack at each location $\sigma_E$—Walker equivalent stress range, accounting for mean stress of a stress cycle during operation The following lookup Tables are provided:

Table 1: a, $\sigma_{ss}$, $t_{ss}$, $\sigma_{mech}$ as a function of N, TCD, PCD Table 2: W as a function of $\sigma_{min}/\sigma_{max}$ Table 3: $\Delta R$ as a function of RA, $\sigma_e$ Table 4: NR as a function of RA It will be appreciated that the total stress for any radial location of a rotating part of the turbine at any time is given by the following equation:

$$\sigma_{tot_{i+1}} = \sigma_{res} + \sigma_{mech_{i+1}} + \sigma_{o_{i+1}} + \sigma_{trans_{i+1}}$$

Also, the thermal or transient stress at any given time in the transient may be approximated by the following equation:

$$\sigma_{trans_{i+1}} = (\sigma_{ss_{i+1}} - \sigma_{o_{i+1}})(a_{i+1}t)^2 / \sqrt{(1 - a_{i+1}^2 t^2)^2 + (a_{i+1}bt)^2}$$

As the machine starts a duty cycle, the compressor discharge temperature $TCD_i$, the compressor discharge pressure $PCD_i$, the rotor speed N, and the time t are read and recorded in memory. If the time interval between the beginning of the new duty cycle $t_i$ and the end of the previous duty cycle $t_o$ is greater than the time necessary for the thermal stress to reach steady state, then the thermal stress $\sigma_{o_i}$ at the beginning of the next duty cycle is 0 as indicated at 30 in FIG. 2a. However, if that time interval is less than the time $t_{ss_o}$ necessary for the thermal stress to reach steady state, then the stress $\sigma_{o_i}$ at the start of the duty cycle may be approximated as the stress at the beginning of the previous transient plus the ratio of the time interval between duty cycles to the time required for the thermal stress of the previous transient to reach steady state multiplied by the difference of the beginning and steady state stresses of the previous transient as in the equation at 32 in FIG. 2a.

At the end of a predetermined time interval, i.e., t=s and after the start of the duty cycle when N>0, a multiplier $a_i$ which is a function of rotor speed, compressor discharge temperature and pressure, the steady state stress $\sigma_{ss_i}$, and the time $t_{ss_i}$ required for the transient stress to approximate the steady state stress are determined. These values and the mechanical stress $\sigma_{mech}$ may be calculated, or provided in lookup Table 1. The multiplier $a_i$ is proportional to the heat transfer coefficient and may be calculated in accordance with the following equation:

$$a_i = \frac{a_p[(N_i)(P_i)]^{.8}}{(t_i)^{.6}}$$

The steady state stress may be calculated from the following equation: $\sigma_{ss_i} = K_p(T_i)$ where $K_p$ is a constant different for each location and is calculated in the initial design stage. The time $t_{ss_i}$ required for the thermal stress $\sigma_{trans}$ to approximate $\sigma_{ss}$ may be calculated from the following equation:

$$t_{ss_i} = \sqrt{\frac{2 - b^2 + \sqrt{b^4 - 4b^2 + 3.628}}{.186\, a_i^2}}$$

The mechanical stress $\sigma_{mech_i}$ is calculated from $\sigma_{mech_i} = \sigma_{mech_p}(N_i/N_p)^2$ or obtained from the lookup Table 1. Thus, the values of the time $t_{ss_i}$ required for the transient stress to equal the steady state stress $\sigma_{ss}$ and the steady state stress $\sigma_{ss_i}$ are calculated and stored. Consequently, the total stress $\sigma_{tot_i}$ at the beginning of the transient and the stress $\sigma_{tot_o}$ at the end of the previous duty cycle are known and recorded as indicated at 34 in FIG. 2a.

Figure 2A:
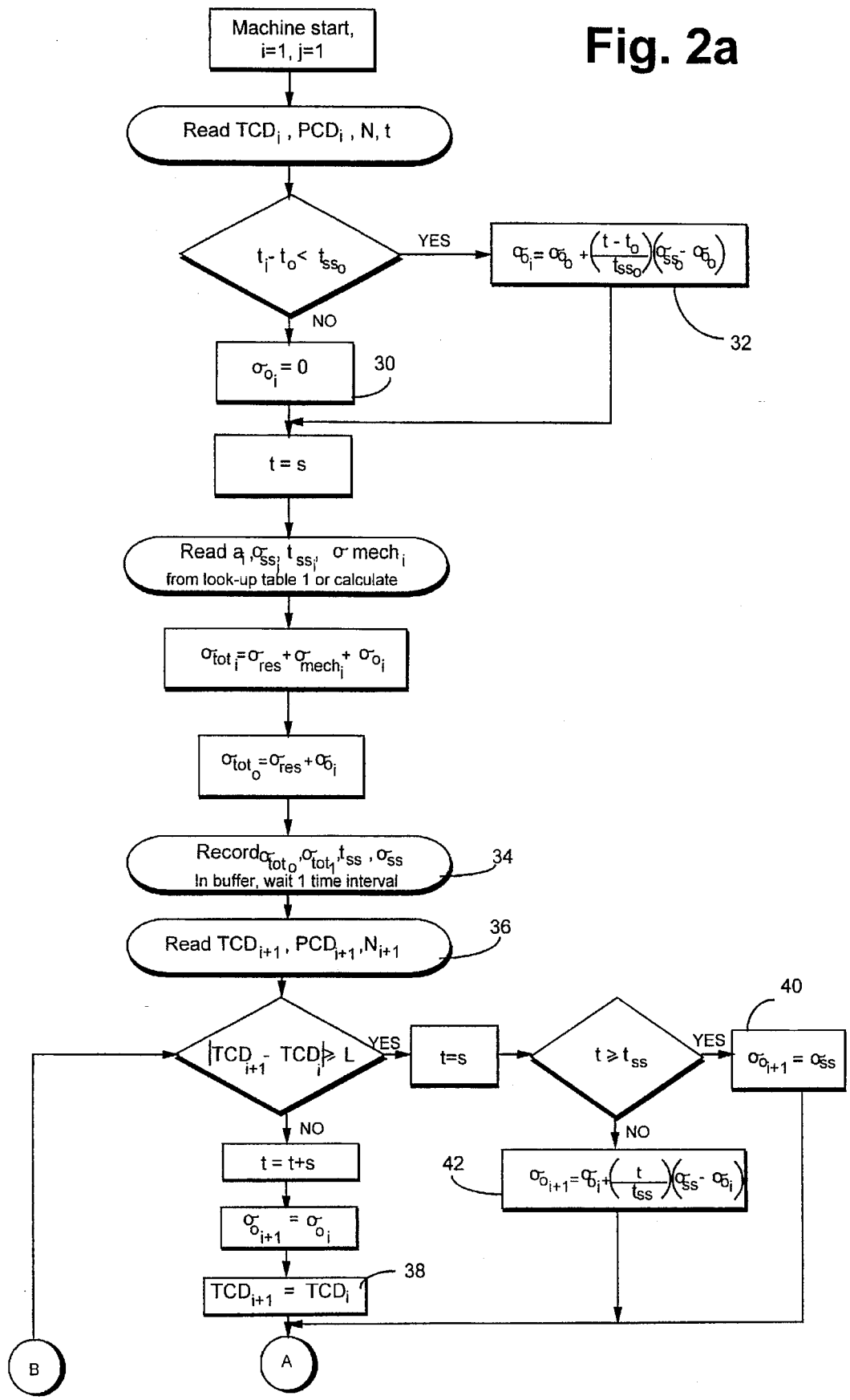
FIGS. 2a–2d are schematic flow diagrams illustrating the various steps for determining the severity of actual duty cycles, the flow diagrams being connected at the letters A, B; C; and D, E.

At the end of a subsequent time interval i+1, the compressor discharge temperature and pressure $TCD_{i+1}$ and $PCD_{i+1}$, respectively, as well as the rotor speed $N_{i+1}$ are read and recorded in the memory as indicated at 36 in FIG. 2a. If the difference between the compressor discharge temperatures at the ends of the previous time interval and the present time interval are less than a value L where the change in thermal stress is insignificant, then the present time interval is considered a continuation of the prior time interval, and the starting stress $\sigma_{o_{i+1}}$ at the start of the time interval will be defined as the stress $\sigma_{o_i}$ at the start of the prior time interval and the compressor discharge temperature will be recorded as identical to the prior recorded temperature as indicated at 38. However, if at the end of the time interval t=s, the change in compressor discharge temperature is significant and the expired time is greater than or equal to the time required for the thermal stress of the transient to approximate the steady state stress at the end of the transient, then the stress at the start of the transient $\sigma_{o_{i+1}}$ is defined as the steady state stress $\sigma_{ss}$ at the end of the previous time interval as indicated at 40 in FIG. 2a. However, if the change in compressor discharge temperature is significant and if the time interval is less than the time required for the transient stress to reach steady state, then the transient stress at the expiration of the time interval will equal the stress $\sigma_{o_i}$ at the start of the transient plus the difference between the steady state stress $\sigma_{ss}$ at the end of the transient and the stress $\sigma_{o_i}$ at the start of the transient, multiplied by the ratio of the time interval to the time required for the transient thermal stress to approximate the steady state thermal stress as indicted at 42 in FIG. 2a. Consequently, at the end of the time interval, the values for $a_{i+1}$, the steady state stress $\sigma_{ss_{i+1}}$, the time $t_{ss_{i+1}}$ required for the stress transient to approximate a steady state and the mechanical stress $\sigma_{mech_{i+1}}$ are calculated or are known from lookup Table 1 as indicated at 44 in FIG. 2b. The transient thermal stress $\sigma_{trans_{i+1}}$ for the time interval i+1 is given by the following equation:

$$\sigma_{trans_{i+1}} = (\sigma_{ss_{i+1}} - \sigma_{o_{i+1}})(a_{i+1}t)^2 / \sqrt{(1 - a_{i+1}^2 t^2)^2 + (a_{i+1}bt)^2}$$

Consequently, the total stress $\sigma_{tot_{i+1}}$ for each location may then be calculated from the following equation:

$$\sigma_{tot_{i+1}} = \sigma_{res} + \sigma_{mech_{i+1}} + \sigma_{o_{i+1}} + \sigma_{trans_{i+1}}$$

Figure 2B:
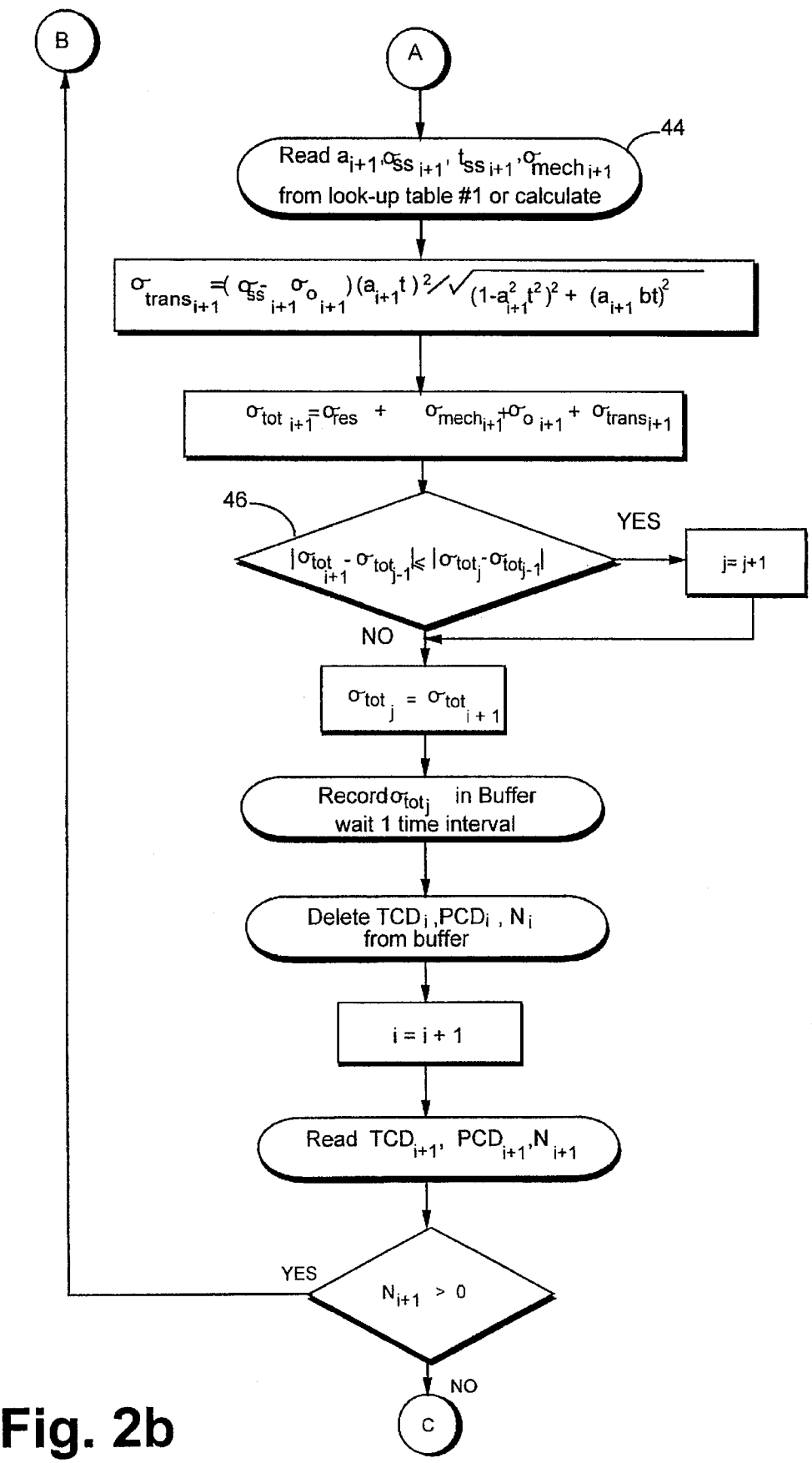

As indicated at 46 in FIG. 2b, if the difference between the total stress $\sigma_{tot_{i+1}}$ and the initial total stress $\sigma_{tot_o}$ is less than the difference between the total stress $\sigma_{tot_i}$ and the total stress $\sigma_{tot_o}$ then the total stresses $\sigma_{tot_i}$ and $\sigma_{tot_{i+1}}$ are recorded in the memory. This retains in memory the old peak or maximum stress and a potential new minimum stress. If the difference is greater, the total stress $\sigma_{tot_i}$ is replaced in the memory with the total stress $\sigma_{tot_{i+1}}$. This retains in memory a new peak stress. Consequently, the total stress $\sigma_{tot_i}$ is recorded in the memory as a new maximum, as corresponding to the old maximum or as a potential minimum, which as explained hereafter, enables calculation of stress intensity factors K.

Figure 3:
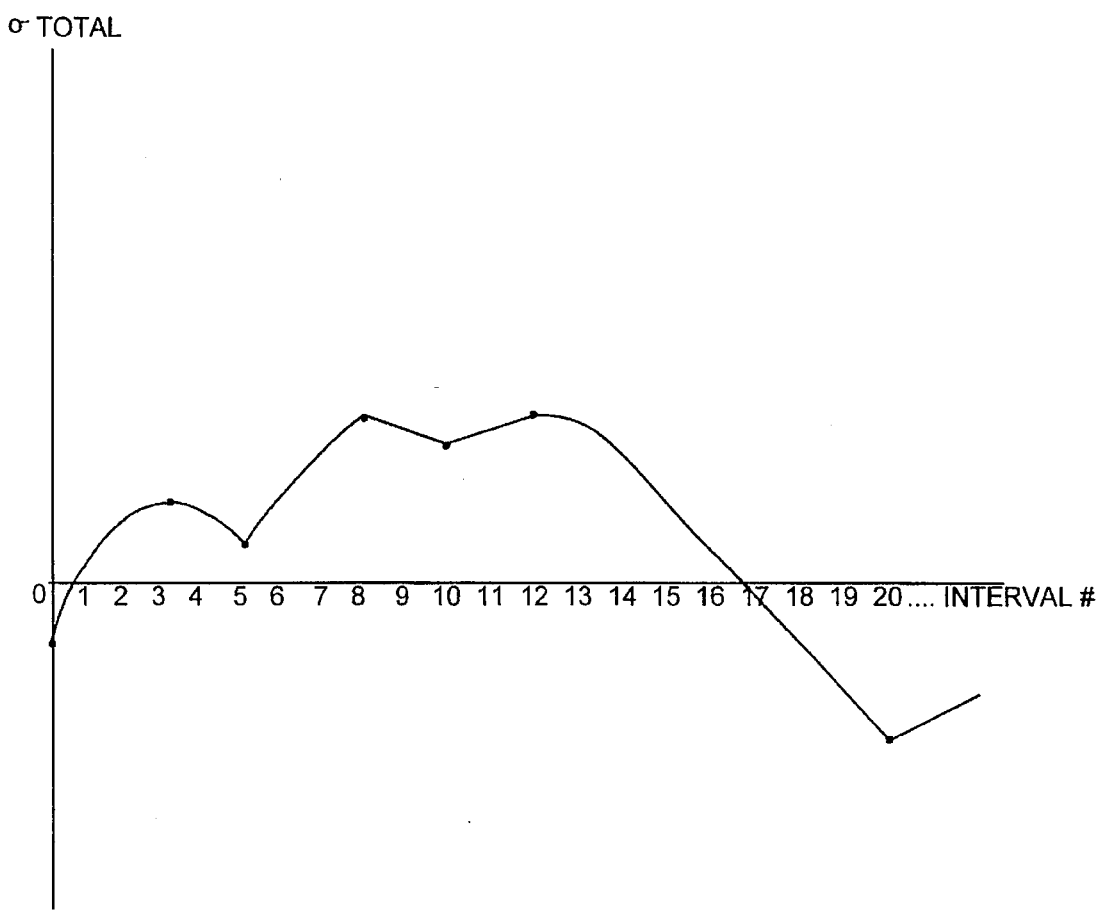
FIG. 3 is a graph representative of maximum and minimum stress peaks during a duty cycle with total stress plotted on the ordinate and time intervals on the abscissa.
Figure 4:
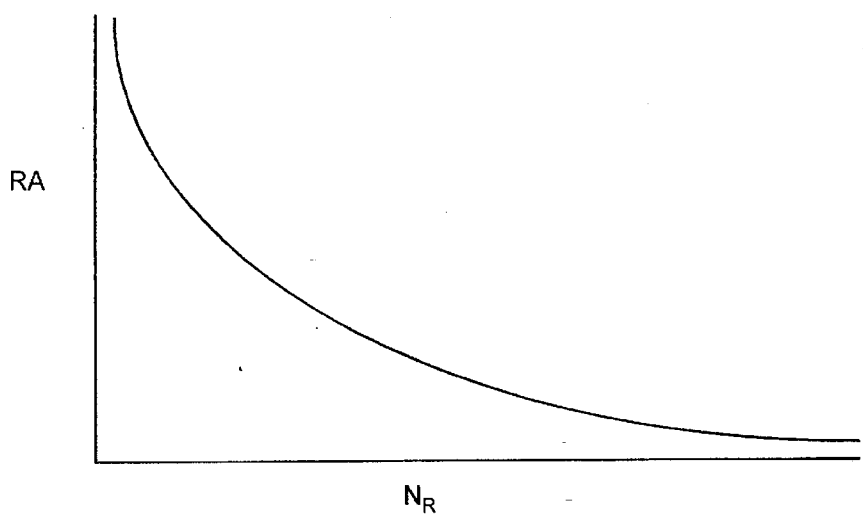
FIG. 4 is a graph representing the length of the assumed crack, RA and the calculated cyclic life $N_R$.

After another time interval, the compressor discharge temperature $TCD_{i+1}$, the compressor discharge pressure $PCD_{i+1}$ and the rotary speed $N_{i+1}$ are recorded. The foregoing described calculations are then repeated at the end of the next time interval as indicated by the line B in FIGS. 2a and 2b and for each subsequent interval during the entire duty cycle. Consequently, over the complete total duty cycle until shutdown (N=O), a plurality of maximum and minimum total stress peaks are recorded in memory. For example, and referring to FIG. 3, a graph shows the maximum and minimum peaks for the total stress versus the time intervals. Knowing the maximum and minimum total stress peaks, an equivalent stress range $\sigma_E$ may be determined.

Figure 2C:
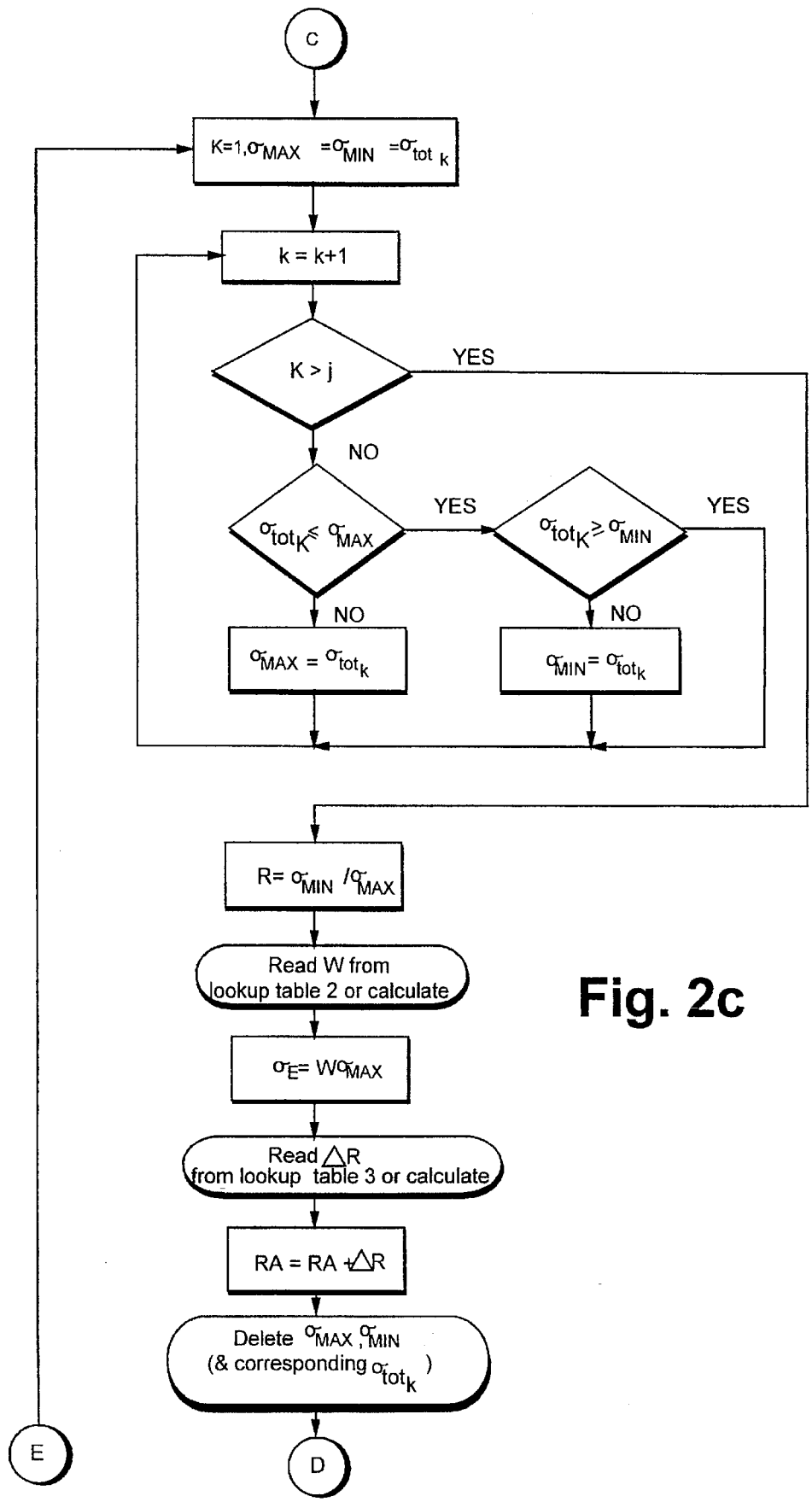

The stress range affects the rate of crack propagation. The equivalent stress range $\sigma_E$ is determined at the end of the duty cycle as in FIG. 2c by identifying the maximum and minimum stress peaks through the duty cycle. For example, if the total stress at the end of a time interval is greater than the last recorded maximum peak stress $\sigma_{max}$ or less than the last recorded minimum peak stress $\sigma_{min}$, such total stress is recorded as a potential new minimum or maximum peak stress, respectively. The total stresses are then sampled at the end of succeeding time intervals until a maximum peak stress or minimum peak stress is identified and recorded. Thus, if the total stress at the end of a predetermined time interval, for example, interval 3 in FIG. 3, corresponds to a maximum peak stress, then the total stress is recorded as the maximum at the end of that time interval. The sampling continues for each subsequent time interval. If the new peak stress is a new maximum value, it is retained as the maximum peak stress, for example, interval 8 of FIG. 3. If the new peak stress is a new minimum value, the new minimum value is recorded. Consequently, over the duty cycle, maximum and minimum peak stresses and stress range ($\hat{\sigma} = \sigma_{max} - \sigma_{min}$) will be recorded. Subsequently, the next largest stress range ($\hat{\sigma}$) is determined in the same manner. This is continued until all local stress peaks have been used to establish the ranges of each stress cycle in the duty cycle.

For each such stress cycle, at each location, the equivalent stress range is calculated. The equivalent stress range $\sigma_E$ is given by $\sigma_E = \hat{\sigma}(W)$ where W represents the Walker mean stress correction, calculated, or from lookup Table 2. A stress intensity factor is calculated using this stress range and the size of the assumed crack using the equation $K = K_p(\sigma_E)\sqrt{RA}$ or using the lookup Table 3. The assumed crack will grow as a function of the stress intensity factor according to the following: $\Delta R = A_p(K)^{n_p}$ where $A_p$ and $n_p$ are recognized as materials constants known as Paris constants. Consequently, by summing the growth $\Delta R$ of the assumed crack between $\sigma_{max}$ and $\sigma_{min}$ and the initial assumed crack and performing this calculation for each $\sigma_{max}$ and $\sigma_{min}$ after deleting the previously used $\sigma_{max}$ and $\sigma_{min}$, the total crack length RA is ascertained.

Figure 2D:
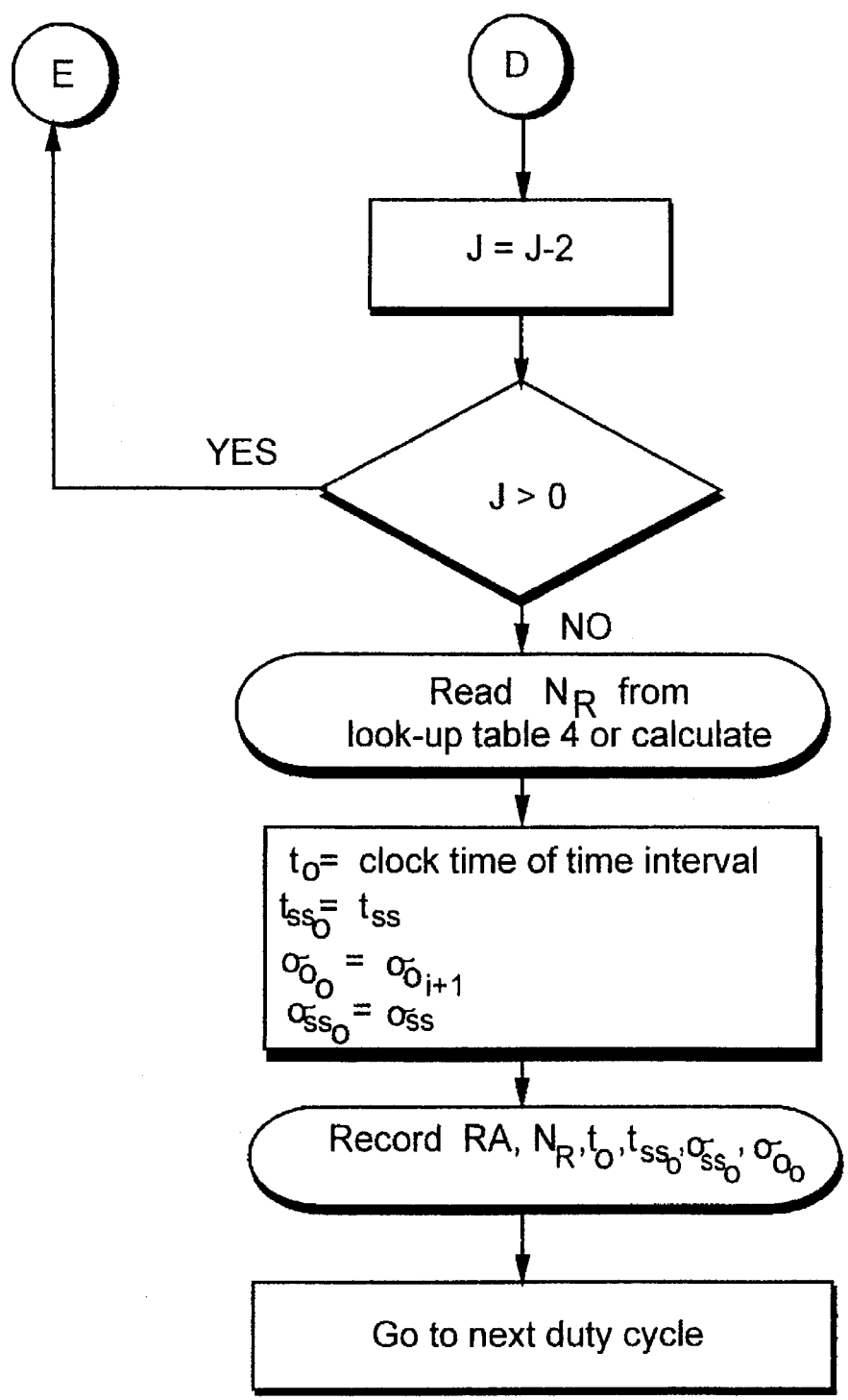

At the end of the duty cycle as illustrated in FIG. 2d, the remaining calculated life for the machine (from lookup Table 4) is determined from the total crack length RA, it being appreciated that the remaining calculated cyclic life may be different from the remaining cyclic life based on the initially calculated cyclic life during the design stages of the machine. This calculation may be provided at the end of each duty cycle or at the end of any number of duty cycles as illustrated in FIG. 2d.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process for determining cyclic service life for rotational parts of a turbine having a compressor, comprising the steps of:

(a) measuring compressor discharge pressure and temperature and speed of a rotational part of said turbine at the end of each of a plurality of time intervals in and commencing at the start of a duty cycle;

(b) determining the total stress on said rotational part at the end of each time interval based on values of said measured pressure, temperature and part speed;

(c) recording, for each time interval, either (i) the total stress on said part as a maximum or minimum value if the total stress for a given time interval is more extreme than a last recorded total stress of a preceding time interval or (ii) the last recorded total stress as a maximum or minimum value if the total stress on said part in said given time interval is less extreme than said last recorded total stress and, if the total stress of Paragraph (c)(ii) is recorded, the total stress on said part as a new minimum or maximum value for said given time interval;

(d) at the end of said duty cycle, determining stress intensity factors using said previously recorded maximum and minimum values of the total stresses;

(e) determining from the stress intensity factors, an aggregate crack propagation value of an assumed crack for said duty cycle; and (f) determining a remaining calculated cyclic life for said machine based on said aggregate crack propagation.

2. A process according to claim 1 wherein the step of determining the total stress at the end of each time interval includes approximating transient stresses in accordance with the following:

$$\sigma_{trans_{i+1}} = \sigma_{o_{i+1}} + \frac{(\sigma_{ss_{i+1}} - \sigma_{o_{i+1}})(a_{i+1}t)^2}{\sqrt{(1 - a_{i+1}^2 t^2)^2 + (a_{i+1}bt)^2}}$$

wherein $\sigma_{trans_{i+1}}$ is the transient thermal stress of said part at the end of a time interval i+1;

$\sigma_{ss_{i+1}}$ is the steady state stress at the end of the transient of time interval i+1;

$\sigma_{o_{i+1}}$ is the stress at the start of the transient i+1;

$a_{i+1}$ is a multiplier proportional to the heat transfer coefficient of said part;

t is time;

b is a geometric constant known for said part;

i+1 is the time interval between measurements of pressure, temperature and speed of rotation at time i and time i+1 and wherein $\sigma_{ss_{i+1}} = K_p(T)$ where $K_p$ is a calculated design constant for said part and T is said compressor discharge temperature.

3. A process according to claim 2 wherein $\sigma_{o_{i+1}}$ is determined in accordance with the following:

$$\sigma_{o_{i+1}} = \sigma_{o_i} + \frac{(t)}{(t_{ss_i})} (\sigma_{ss_i} - \sigma_{o_i})$$

where $t_{ss_i} =$ $$\frac{\sqrt{2 - b^2 + \sqrt{b^4 - 4b^2 + 3.628}}}{.186 a^2}.$$

4. A process according to claim 2 wherein $\sigma_{o_{i+1}}$ is equal to $\sigma_{ss_i}$ if the difference in compressor discharge temperatures at the end of times i+1 is greater than a predetermined magnitude and the time interval between times i and i+1 is greater than the time required for the transient stress to equal steady state stress.

5. A process according to claim 2 wherein the step of determining the total stress is accomplished according to the following:

$$\sigma_{tot_i} = \sigma_{Res_p} + \sigma_{mech} \left( \frac{Ni}{Np} \right)^2 + \sigma_{trans_i}$$

wherein $\sigma_{Res_p}$ is the calculated residual stress for said part $\sigma_{mech}$ is the calculated mechanical stress for said part at a design speed of rotation of $N_p$ and $N_i$ is the actual speed at any given time of the rotating part in said duty cycle.

6. A process according to claim 1 including, at start-up of said duty cycle, determining the total stress, from any previous duty cycle and record the total stress of said previous duty cycle.

7. A process according to claim 1 wherein the stress intensity factors are determined by determining differences between maximum and minimum recorded total stress values starting with the maximum difference and successively determining the next maximum difference between maximum and minimum values until zero differences remain, and multiplying each difference by a constant.

8. A process according to claim 7 wherein the step of determining the aggregate crack propagation value includes determining a crack propagation value for each stress intensity factor and aggregating the determined stress propagation values.

* * * * *